United States Patent
Manica et al.

(10) Patent No.: US 10,593,422 B2
(45) Date of Patent: Mar. 17, 2020

(54) INTERACTION NETWORK INFERENCE FROM VECTOR REPRESENTATION OF WORDS

(71) Applicant: International Business Machines Corporation, Armonk, NY (US)

(72) Inventors: Matteo Manica, Zürich (CH); Roland Mathis, Zürich (CH); Maria Rodriguez Martinez, Thalwill (CH); Konstantinos Bekas, Horgen (CH)

(73) Assignee: International Business Machines Corporation, Armonk, NY (US)

( * ) Notice: Subject to any disclaimer, the term of this patent is extended or adjusted under 35 U.S.C. 154(b) by 130 days.

(21) Appl. No.: 15/829,123

(22) Filed: Dec. 1, 2017

(65) Prior Publication Data

US 2019/0171792 A1    Jun. 6, 2019

(51) Int. Cl.
| | |
|---|---|
| *G16B 40/00* | (2019.01) |
| *G06K 9/62* | (2006.01) |
| *G16B 15/00* | (2019.01) |
| *G06F 16/35* | (2019.01) |
| *G06F 40/20* | (2020.01) |
| *G06F 40/30* | (2020.01) |

(Continued)

(52) U.S. Cl.
CPC ........... *G16B 40/00* (2019.02); *G06F 16/355* (2019.01); *G06F 40/20* (2020.01); *G06F 40/216* (2020.01); *G06F 40/284* (2020.01); *G06F 40/30* (2020.01); *G06K 9/6223* (2013.01); *G06K 9/6276* (2013.01); *G16B 15/00* (2019.02)

(58) Field of Classification Search
CPC ..... G06F 17/2785; G06F 17/27; G16B 40/00; G16B 50/00

USPC .............................................. 704/9
See application file for complete search history.

(56) References Cited

U.S. PATENT DOCUMENTS

| 9,542,528 B2 | 1/2017 | Zhang | |
|---|---|---|---|
| 2013/0073571 A1* | 3/2013 | Coulet | G16B 50/00 707/755 |

(Continued)

FOREIGN PATENT DOCUMENTS

| CN | 104391963 A | 3/2015 |
|---|---|---|

OTHER PUBLICATIONS

Quan et al., "An Unsupervised Text Mining Method for Relation Extraction from Biomedical Literature", PLOS ONE, www.plosone.org, Jul. 2014, vol. 9, Issue 7; pp. 1-8.

(Continued)

*Primary Examiner* — Jakieda R Jackson
(74) *Attorney, Agent, or Firm* — Scully, Scott, Murphy & Presser, P.C.; Daniel Morris, Esq.

(57) ABSTRACT

The present disclosure relates to a system and method for extracting information from text data. The method comprises: obtaining a plurality of text elements. A word embedding algorithm may be applied to the obtained text elements by mapping each text element of at least part of the text elements into a vector of a predefined dimension. The mapped text elements may be clustered into groups using the distances between the respective vectors. For each text element of a set of text elements of the mapped text elements a respective distribution of neighbors across the groups may be built. Similarity scores may be computed using the distributions thereby for determining relations between the set of text elements.

18 Claims, 4 Drawing Sheets

(51) Int. Cl.
    *G06F 40/216* (2020.01)
    *G06F 40/284* (2020.01)

(56) References Cited

U.S. PATENT DOCUMENTS

2016/0203256 A1    7/2016   Chen
2016/0352591 A1*   12/2016  Sasturkar .............. H04L 43/045
2017/0024476 A1    1/2017   Gramatica

OTHER PUBLICATIONS

Hu et al., "Data mining and predictive modeling of biomolecular network from biomedical literature databases", IEEE/ACM Transactions on Computational Biology and Bioinformatics, Apr.-Jun. 2007; vol. 4, No. 2; pp. 251-263.

Peng et al., "Cross-Sentence N-ary Relation Extraction with Graph LSTMs", Transactions of the Association for Computational Linguistics, vol. 5, pp. 101-115, Submission batch: Oct. 2016; Revision batch: Apr. 2017; Published: Apr. 2017.

* cited by examiner

INTERACTION NETWORK INFERENCE FROM VECTOR REPRESENTATION OF WORDS

BACKGROUND

The present invention relates to the field of digital computer systems, and more specifically, to a method to extract information from text data.

The number of scientific publications is growing exponentially and search engines such as PubMed make available huge amounts of information in the form of unstructured written language. As of January 2017, PubMed comprises more than 26 million citations for biomedical literature from MEDLINE, life science journals, and online books. Citations may include links to full-text content from PubMed Central (PMC) and publisher web sites. The numbers remain high even when focusing on specific fields of biomedical research, such as prostate cancer. For instance, a simple query for prostate cancer related papers on PMC can return a list of over 180000 publications. In order to fully exploit this rich corpus of written knowledge, the development of new techniques that can automatically extract facts and knowledge, manipulate the data and produce summarized representations that captures specific information are required.

SUMMARY

Various embodiments provide a method to extract information from text data, computer system and computer program product as described by the subject matter of the independent claims. Advantageous embodiments are described in the dependent claims. Embodiments of the present invention can be freely combined with each other if they are not mutually exclusive.

In one aspect, the invention relates to a computer implemented method to extract information from text data. The method comprises:
 obtaining a plurality of text elements;
 applying a word embedding algorithm to the obtained text elements comprising mapping each text element of at least part of the text elements into a vector of a predefined dimension;
 clustering the mapped text elements into groups using the distances between the respective vectors;
 building for a set of text elements of the mapped text elements a respective distribution of neighbors across the groups;
 computing similarity scores using the distributions thereby determining relations between the set of text elements.

In another aspect, the invention relates to a computer program product comprising a computer-readable storage medium having computer-readable program code embodied therewith, the computer-readable program code configured to implement all of steps of the method according to preceding embodiments.

In another aspect, the invention relates to a computer system to extract information from text data. The computer system is configured for:
 obtaining a plurality of text elements;
 applying a word embedding algorithm to the obtained text elements comprising mapping each text element of at least part of the text elements into a vector of a predefined dimension;
 clustering the mapped text elements into groups using the distances between the respective vectors;
 building for a set of text elements of the mapped text elements a respective distribution of neighbors across the groups;
 computing similarity scores using the distributions thereby determining relations between the set of text elements.

BRIEF DESCRIPTION OF THE SEVERAL VIEWS OF THE DRAWINGS

In the following embodiments of the invention are explained in greater detail, by way of example only, making reference to the drawings in which.

DETAILED DESCRIPTION

Figure 1:
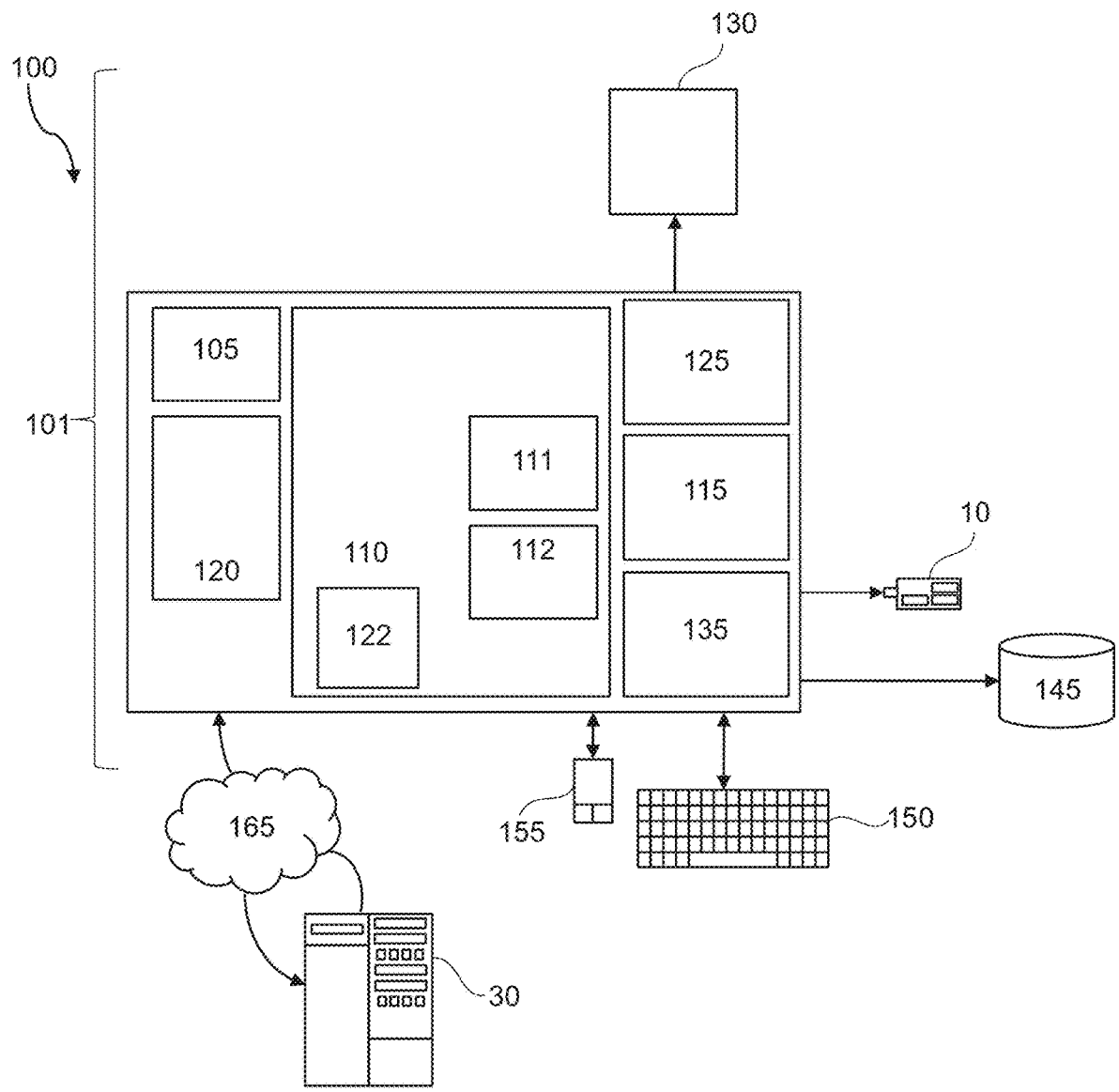
FIG. 1 represents a computerized system, suited for implementing one or more method steps as involved in the present disclosure.

The descriptions of the various embodiments of the present invention will be presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present method may enable to automatically extract facts e.g. from the biomedical literature in order to better understand the molecular relationships underlying complex diseases such as prostate cancer (PC). The current prognostic factors are not sufficient and thus PC is prone to overdiagnosis, associated with large and debilitating side effects. The present method may enable a better understanding of the complex molecular mechanisms underlying PC development and progression, potentially reducing overdiagnosis and opening improved treatment scenarios. The present method may further be advantageous as it is based on a totally unsupervised approach such as comparing neighbors distributions of vectors obtained from a word embedding algorithm to build context-specific molecular interaction networks from unstructured text. There may be no need for manual curation and labelling of the text and no annotations or other manual processing steps may be required. And the results may be obtained without optimization of hyperparameters.

The volume of information that can be extracted from publications greatly exceeds the information currently stored in public databases. Furthermore, the rate at which new research articles are published greatly exceeds the rate at which this information can be processed by curated databases, which means that the gap between available knowledge and information stored in databases will only become wider. The present method may provide solution to that problem as it may enable to automatically analyze unstructured documents and extract relevant information in an efficient manner. The present method may provide a learning framework to automatically extract information such as molecular interactions from unstructured text in an unsupervised manner.

The obtained text elements may form a so-called text corpus. For example, a word embedding algorithm may first be used as an unsupervised learning method to build a vector space (also referred to as word embedding space) of vectors of the text elements. The word embedding space may be of several hundred dimensions, where each unique text element is represented as a vector. In this representation, text elements that share a similar context in the corpus are located in close proximity in the vector space. Next, the vectors may be clustered, using K-means algorithm in the vector space, into groups of text elements conveying semantic and contextual similarity. The groups may be used to evaluate the similarity between two text elements. The similarity is computed looking at text elements neighborhood, evaluating the distribution of the neighbors across groups. For example, the text elements may be obtained from a biomedical content and may thus be used to predict protein-protein interactions based on the similarity measure of protein pairs.

The term text element can refer to, but is not limited to, one or more characters, symbols, words, strings of characters, emoticons, numbers, formulas, sentences, or paragraphs.

The word embedding (also referred to as word embedding algorithm) may comprise a family of methods that produce, starting from a text corpus, a real vector representation of each text element. Word embedding methods take a text corpus (e.g. the obtained text elements) as input, construct a vocabulary from training text data, learn vector representation of text elements and deliver the vectors as output. Words that appear in similar contexts have similar meaning. Vector representation allows to perform vector operations such as finding shortest distance between words.

According to one embodiment, the set of text elements comprising names of molecular entities. The method further comprises building a molecular interaction network using the similarity scores. This embodiment may enable an automatic and efficient method for extracting molecular interactions.

A molecular entity refers to a constitutionally or isotopically distinct atom, molecule, ion, ion pair, radical, radical ion, complex, conformer, etc., identifiable as a separately distinguishable entity. The molecular interaction network comprises molecular entities as nodes and the molecular interactions as edges. The molecular interaction network may indicate physical interactions among molecules such as those among proteins, also known as protein—protein interactions, (PPIs) and/or indirect interactions among genes (genetic interactions) as described in the text corpus of the obtained text elements. The similarity score between two text elements may be indicative of the physical interaction between the two text elements. The higher the similarity score the more the interaction is supported by the algorithm. For example, the molecular entities that interact with each other and are involved in similar biological processes may appear in similar word contexts, and thus may be mapped to neighboring positions resulting from the application of the word embedding algorithm. One can thus predict functional similarities between genes or proteins based on their proximity in the word embedding space. The present method may provide optimal ways of measuring proximity between text elements in the word embedding space. The similarity score may be a measure of how confident an interaction exists. The similarity score between two text elements may be calculated as the similarity score between the respective distributions of the two text elements.

According to one embodiment, the method further comprises providing a vocabulary of text elements, wherein the set of text elements are present in both the mapped text elements and the vocabulary.

According to one embodiment, the building of the distribution for a given text element comprises: identifying a predefined number of nearest neighbors of the given text element; determining the group to which belongs each of the identified nearest neighbors, wherein the distribution for the given text element indicates for each determined group the fraction of nearest neighbors of the identified nearest neighbors that belong to the determined group over the predefined number of nearest neighbors. This may provide a systematic and accurate method for defining the context of a text element.

According to one embodiment, identifying the nearest neighbors comprises building a k-d tree of the vectors representing the text elements and using the k-d tree for identifying the nearest neighbors. This embodiment may provide an efficient method to retrieve the topological neighbors without having to compute all pairwise distances at each query.

According to one embodiment, the predefined number of nearest neighbors is determined based on the number of groups. For example, the number of nearest neighbors may be a fixed or may dynamically be determined based on the clustering algorithm being used. This may enable a systematic fine grained word representation based on the clustering being used.

According to one embodiment, the obtaining of the text data comprises: querying a predefined database for one or more documents; parsing the queried documents for extracting text; identifying in the extracted text at least one of bi-grams, trigrams, words and a combination thereof for obtaining the text elements.

According to one embodiment, the vectors are word context vectors, wherein the word embedding algorithm involves a skip-gram algorithm. For example, the word embedding algorithm may be the Word2Vec algorithm. The skip-gram may enable to find an optimal representation to predict the surrounding context of a target word. For example, in the following sentence "and some mutations destabilize PTEN and promote PI3K pathway", the target word, PTEN (a gene implicated in many cancer processes) is linked to each of its neighboring words and the pairs are fed into the network. The learning process optimizes the probability of predicting the contextual words of PTEN.

According to one embodiment, the similarity scores are Jensen-Shannon divergence, JSD, scores which are computed for pairs of the built distributions.

According to one embodiment, the clustering is performed using a K-means algorithm.

According to one embodiment, the predefined dimension is 100-1000 or 500. The definition of the dimension may be a trade-off between the richness of the representation requiring high dimensionality and the efficiency of the computation requiring low dimensionality.

According to one embodiment, the text elements form un-structured data. This may enlarge the sample of data on which the present method may be applied.

According to one embodiment, the method is automatically performed. This may speed up the processing of the present method.

FIG. 1 represents a general computerized system, suited for implementing method steps as involved in the disclosure.

It will be appreciated that the methods described herein are at least partly non-interactive, and automated by way of computerized systems, such as servers. In exemplary embodiments though, the methods described herein can be implemented in a (partly) interactive system. These methods can further be implemented in software 112, 122 (including firmware 122), hardware (processor) 105, or a combination thereof. In exemplary embodiments, the methods described herein are implemented in software, as an executable program, and is executed by a special or general-purpose digital computer, such as a personal computer, workstation, minicomputer, or mainframe computer. The most general system 100 therefore includes a general-purpose computer 101.

In exemplary embodiments, in terms of hardware architecture, as shown in FIG. 1, the computer 101 includes a processor 105, memory (main memory) 110 coupled to a memory controller 115, and one or more input and/or output (I/O) devices (or peripherals) 10, 145 that are communicatively coupled via a local input/output controller 135. The input/output controller 135 can be, but is not limited to, one or more buses or other wired or wireless connections, as is known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components. As described herein the I/O devices 10, 145 may generally include any generalized cryptographic card or smart card known in the art.

The processor 105 is a hardware device for executing software, particularly that stored in memory 110. The processor 105 can be any custom made or commercially available processor, a central processing unit (CPU), an auxiliary processor among several processors associated with the computer 101, a semiconductor based microprocessor (in the form of a microchip or chip set), a macroprocessor, or generally any device for executing software instructions.

The memory 110 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM). Note that the memory 110 can have a distributed architecture, where various components are situated remote from one another, but can be accessed by the processor 105.

The software in memory 110 may include one or more separate programs, each of which comprises an ordered listing of executable instructions for implementing logical functions, notably functions involved in embodiments of this invention. In the example of FIG. 1, software in the memory 110 includes instructions 112 e.g. instructions to manage databases such as a database management system. The memory 110 may further comprise a query optimizer. The query optimizer may comprise instructions e.g. software instructions that when executed may provide a query execution plan for executing a given query.

The software in memory 110 shall also typically include a suitable operating system (OS) 111. The OS 111 essentially controls the execution of other computer programs, such as possibly software 112 for implementing methods as described herein.

The methods described herein may be in the form of a source program 112, executable program 112 (object code), script, or any other entity comprising a set of instructions 112 to be performed. When a source program, then the program needs to be translated via a compiler, assembler, interpreter, or the like, which may or may not be included within the memory 110, so as to operate properly in connection with the OS 111. Furthermore, the methods can be written as an object oriented programming language, which has classes of data and methods, or a procedure programming language, which has routines, subroutines, and/or functions.

In exemplary embodiments, a conventional keyboard 150 and mouse 155 can be coupled to the input/output controller 135. Other output devices such as the I/O devices 145 may include input devices, for example but not limited to a printer, a scanner, microphone, and the like. Finally, the I/O devices 10, 145 may further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The I/O devices 10, 145 can be any generalized cryptographic card or smart card known in the art. The system 100 can further include a display controller 125 coupled to a display 130. In exemplary embodiments, the system 100 can further include a network interface for coupling to a network 165. The network 165 can be an IP-based network for communication between the computer 101 and any external server, client and the like via a broadband connection. The network 165 transmits and receives data between the computer 101 and external systems 30, which can be involved to perform part or all of the steps of the methods discussed herein. In exemplary embodiments, network 165 can be a managed IP network administered by a service provider. The network 165 may be implemented in a wireless fashion, e.g., using wireless protocols and technologies, such as WiFi, WiMax, etc. The network 165 can also be a packet-switched network such as a local area network, wide area network, metropolitan area network, Internet network, or other similar type of network environment. The network 165 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 101 is a PC, workstation, intelligent device or the like, the software in the memory 110 may further include a basic input output system (BIOS) 122. The BIOS is a set of essential software routines that initialize and test hardware at startup, start the OS 111, and support the transfer of data among the hardware devices. The BIOS is stored in ROM so that the BIOS can be executed when the computer 101 is activated.

When the computer 101 is in operation, the processor 105 is configured to execute software 112 stored within the memory 110, to communicate data to and from the memory 110, and to generally control operations of the computer 101 pursuant to the software. The methods described herein and the OS 111, in whole or in part, but typically the latter, are read by the processor 105, possibly buffered within the processor 105, and then executed.

When the systems and methods described herein are implemented in software 112, as is shown in FIG. 1, the methods can be stored on any computer readable medium, such as storage 120, for use by or in connection with any computer related system or method. The storage 120 may comprise a disk storage such as HDD storage.

Figure 2:
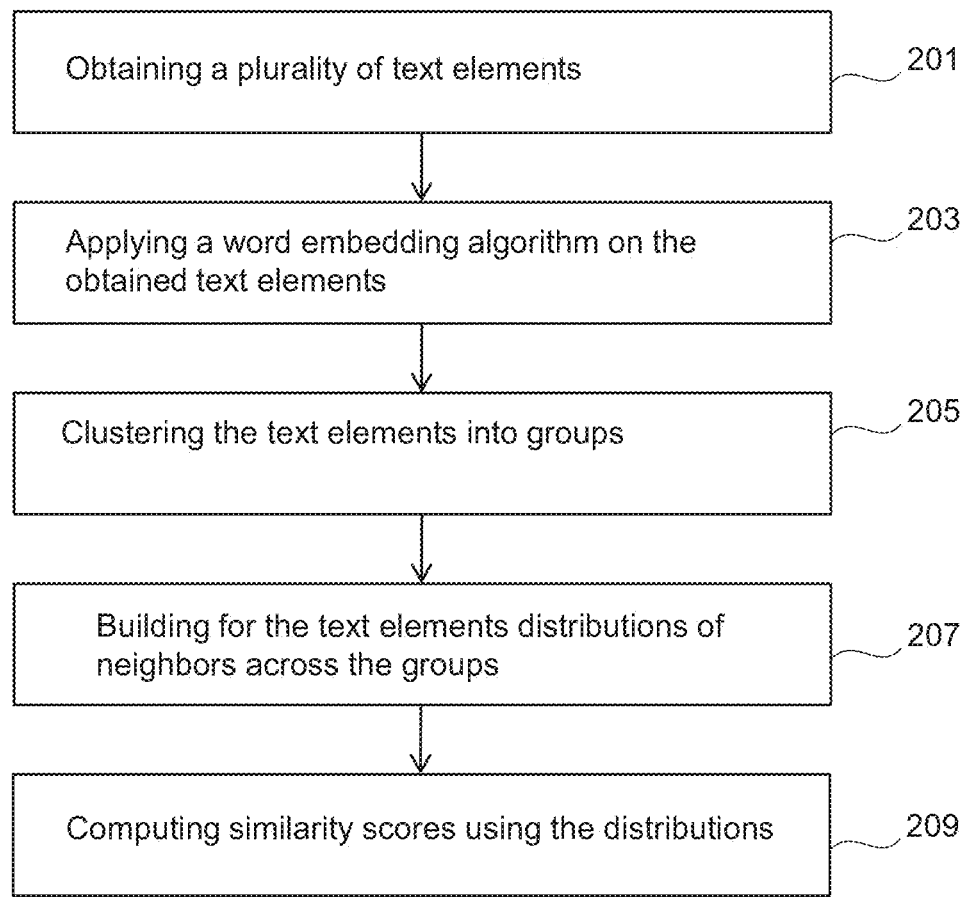
FIG. 2 is a flowchart of a method for extracting information from text data.

FIG. 2 is a flowchart of a method to extract information from text data.

In step 201, a plurality of text elements may be obtained. The text elements may for example relate to biomedical contexts or other contexts. For example, documents related to prostate cancer may be retrieved from PubMed Central (PMC) database using the following query: "(prostate or prostatic) and cancer". This may result in a given number of papers that have content related to the prostate or prostatic and cancer. The papers may be downloaded using the PMC FTP service e.g. in xml format e.g. using computer system 100. The downloaded papers may be parsed to extract text from the papers (e.g. to extract all the abstracts of the papers).

The extracted text may be processed in order to obtain the text elements. The processing of the extracted text may for example comprise: conversion of characters of the extracted to lower-case and/or filtering out non informative words such as extremely common words (e.g. a, the, and, other stop-words), and/or filtering out rare words (e.g. words having a low occurrence in the extracted text, e.g. <=50) and/or filtering out non-informative characters (e.g. punctuation, isolated numbers, etc). The processing may further comprise identification of bi-grams and tri-grams by summing up the occurrences of two (three) words in the case of bi-grams (in the case of tri-grams) appearing next to each other in the extracted text. A threshold of the minimal number of occurrence of bi-grams and tri-grams may be set (e.g. same threshold used as for single words e.g. <=50).

The processing of the extracted text results in single words, bi-grams and tri-grams. The text elements may comprise those resulting single words, bi-grams and tri-grams.

For example, sentences may be generated using an English language tokenizer (e.g. a software used to segment a text into linguistic units such as sentences) before punctuation was removed. The result of this process is a corpus of sentences extracted from the papers that can be used to learn a vector representation for each word using a word embedding algorithm. The text elements may further comprise the sentences.

In step 203, a word embedding algorithm may be applied on the obtained text elements. This may for example comprise mapping each text element of at least part of the obtained text elements into a respective vector in a vector space (or vector representation space) of a predefined dimension. The obtained text elements may be represented as vectors of real numbers in the vector space. The vector representing a given text element may correspond to word neighboring context. The context of the given text element may be defined by other text elements that appear in its surrounding, either in a short window around it, or within the same sentence, paragraph or document.

For example, the Word2Vec algorithm may be used as a training algorithm, a shallow, two-layer neural networks based on a skip-gram model. The skip-gram model aims at predicting the surrounding words of a word given as an input. For example, a window of size 2k+1 (where k is the number of text elements or the size of the window to the left or right of a given text element) may be defined to the left and the right of each target word in order to define a word context. Each target word is mapped to its surrounding words within the window, and the pairs target-neighboring word are fed into the neural network. The network is then trained to optimize the probability of a word w given its context. This learning process is thus optimized to capture the semantic meaning conveyed by contextual words. The dimensionality of the vectors may be set to be between 100 and 1000. Preferably a dimensionality of 500 may be used. That means that for each word a 500-dimensional real vector may be learned. The chosen dimensionality may increase the quality of the word embedding without reaching a critical point where marginal gain diminishes.

The application of the word embedding algorithm may result in n text elements being mapped to respective vectors of dimension d e.g. d=500. The n text elements may be smaller or equal the number of the obtained text elements in step 201. For example, if a text element occurs multiple times in the obtained text elements it may not have multiple corresponding vectors i.e. a text element is mapped to a single vector.

In step 205, the text elements that have been mapped to respective vectors may be clustered into groups using the distances between the respective vectors.

For example W may be defined as the set of the n text elements present in the vector space $\varepsilon \in \mathbb{R}^{n \times d}$ where d is the vector's dimension, e.g. d=500. The clustering of then text elements may be performed using, for example, a K-means algorithm with C groups in the vector space. The number of groups may be predefined e.g. user predefined. The number of groups may for example be defined based on the number of text elements to be clustered. For example, if n=25000, the number of groups C may be chosen equal to 500 in order to have a fine grained word representation. Each text element may hence be associated with a group according to the following mapping: CL: $\mathcal{W} \rightarrow \{1, \ldots, C\}$. The obtained groups group together text elements that are close in the vector representation space, and hence share similar contexts.

In step 207, for each text element of a set of text elements of the mapped text elements a respective distribution (or probability distribution) of neighbors across the groups may be built. The set of text elements may comprise at least part of the n text elements that have been mapped to respective vectors in step 203. For example, the set of text elements may be target text elements selected or identified by a user. This step may enable to associate each text element in the vector space with a discrete probability distribution representing its meaning.

The building of the distribution (e.g. for building word fingerprints) of each of text element of the set of text elements may comprise finding nearest neighbors of the each text element. The nearest neighbors of a given text element may be retrieved as the topological neighbors of the given text element without having to compute all pairwise distances using k-d tree. The nearest neighbor search may be defined as: KNN: $\mathcal{W} \rightarrow \mathcal{N}$, where N is the set of K neighbors for the text elements in the vector space. This may provide the shortest paths between different text elements in the representation space and a fast way to retrieve the nearest text elements.

For example, a predefined number (e.g. 2000) of nearest neighbors may be selected for each text element of the text elements. The definition of the number of nearest neighbors may be driven by the number of groups C (e.g. 2000 nearest neighbors for C=500), in order to obtain a sufficient number of samples to describe the neighbors distribution across the groups, and analyze their group assignment.

The discrete probability distribution of a given text element may be indicative of the number and group occupancy of the neighbors and may convey a richer semantic meaning of the given text element. Comparison of the distributions may enable to define similarities between text elements.

Figures 3A, 3B:
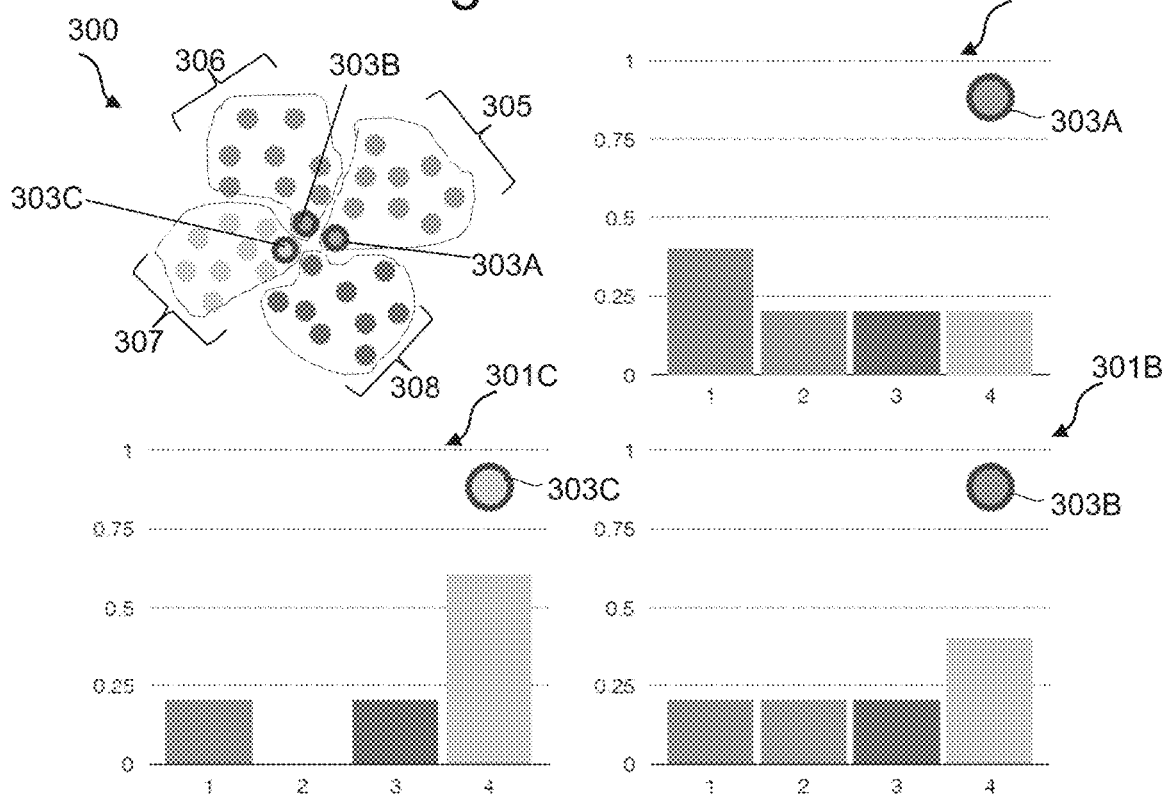
FIG. 3A depicts an algorithm for generating probability distributions in accordance with the present disclosure.
FIG. 3B depicts examples of probability distributions in accordance with the present disclosure.

In step 209, similarity scores may be computed using the distributions thereby determining relations between text elements of the set of text elements. For example, pairs (e.g. all possible pairs) of the distributions may be determined. The similarity scores may be computed between each pair of the determined pairs of the distributions for indicating the similarity between the text elements of the each pair. The similarity scores are indicative of the similarity between the respective distributions (or the respective text elements). FIGS. 3A-B provide examples of the score computation.

In one example, the text elements may indicate the names of the molecular entities e.g. the text elements may be obtained from biomedical documents. Using the computed similarity scores an interaction graph between molecular entities of interest (e.g. proteins) may be built, where the nodes are the chosen entities or text elements between which the similarity scores are computed and the edges are weighted by the similarity value of the nodes they connect.

FIGS. 3A-3B illustrates an example method for generating the distributions, in accordance with step 207, for text elements w belonging to the set $\mathcal{W}$.

The distributions of the predefined text elements may be built using the algorithm of FIG. 3A. The algorithm of FIG. 3A may receive as input the set $\mathcal{W}$, the CL and KNN defined above. The function CL may indicate the group to which belongs a given text element. The function KNN may be configured to provide nearest neighbor list for a given text element. The output of the algorithm is a matrix of probability distributions $\mathcal{D} \in \mathbb{R}^{n \times C}$ where each row contains the group assignments of each target text element.

FIG. 3B illustrates an example of probability distributions 301A-C obtained for respective set of text elements 303A-C. The distributions 301A-C are normalized distributions. Graph 300 of FIG. 3B illustrates the vector space (or word embedding space) indicating the groups resulting from the clustering (e.g. clustering step 205). Graph 300 illustrates four groups 305-308. The predefined text elements 303A-C belong respectively to groups 305, 306 and 307.

For visualization purposes the vector space of text elements is shown in a two-dimensional space in graph 300 where each text element is a dot and the enclosing circles indicate the group membership of each text element. The numbers 1-4 in each of the distributions 301A-C refers to the groups 306, 305, 308 and 307 respectively.

Three text elements (e.g. molecule names) 303A-C were selected and the distributions 301A-C of the neighbors of each of these three text elements 303A-C are shown in FIG. 3B. The distributions 301A-C may be calculated by counting and normalizing the group membership of the five nearest neighbors of each of the selected text elements 303A-C. E.g. for the molecule indicated by the text element 303A the majority of the nearest neighbors belong to the group 306.

The similarities between the text elements of interest (e.g. selected text elements 303A-C), may be computed using a score based on the Jensen-Shannon divergence (JSD) between respective distributions 301A-C, which may be defined as follows:

$$JSD(P\|Q) = \tfrac{1}{2} D_{KL}(P\|M) + \tfrac{1}{2} D_{KL}(Q\|M)$$

Where P and Q are probability distributions, $M=\tfrac{1}{2}(P+Q)$ and $D_{KL}$ is the Kullback-Leibler divergence for discrete probability distributions:

$$D_{KL}(P\|Q) = \sum_i P(i) \log\left(\frac{P(i)}{Q(i)}\right)$$

Where the sum may be over the bins i of the distributions (e.g. the 4 bins numbered 1 to 4 in distributions 301A-C). In addition of providing a symmetrized version of the Kullback-Leibler divergence, JSD may have other useful features such as always being a finite value between $[0, \infty)$, where the lowest bound being reached when the two distributions are identical. The square root of the Jensen-Shannon divergence is a metric, and thus JSD may be an appropriate function to capture similarities between distributions.

In another example, a reciprocal of JSD (IJSD) may be used to define a similarity between text elements. Namely, the reciprocal may be defined as $IJSD(\mathcal{D}_i, \mathcal{D}_j) = JSD(\mathcal{D}_i, \mathcal{D}_j)^{-1}$, and scale in between $[0, 1]$ for pairwise comparisons of text elements. The similarity score $S_{ij}$ between text elements i and j may be computed as follows:

$$S_{ij} = \frac{V_{ij} - \min_{i,j} V}{\max_{i,j} V - \min_{i,j} V}$$

Where $V_{ij} = IJSD(\mathcal{D}_i, \mathcal{D}_j)$ and $V = [V_{ij}]_{j<i}$ is a lower triangular matrix.

Figure 4A:
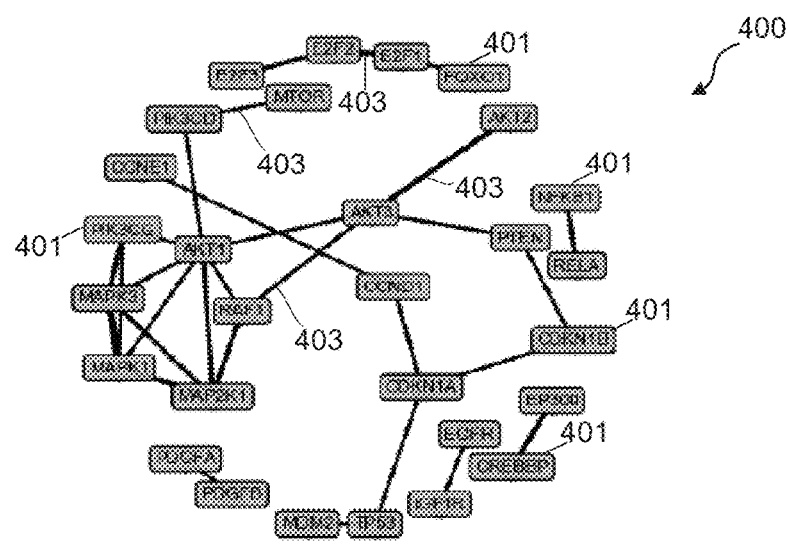
FIG. 4A depicts a molecular interaction graph which results from applying the present method on text elements obtained from prostate cancer publications
Figure 4B:
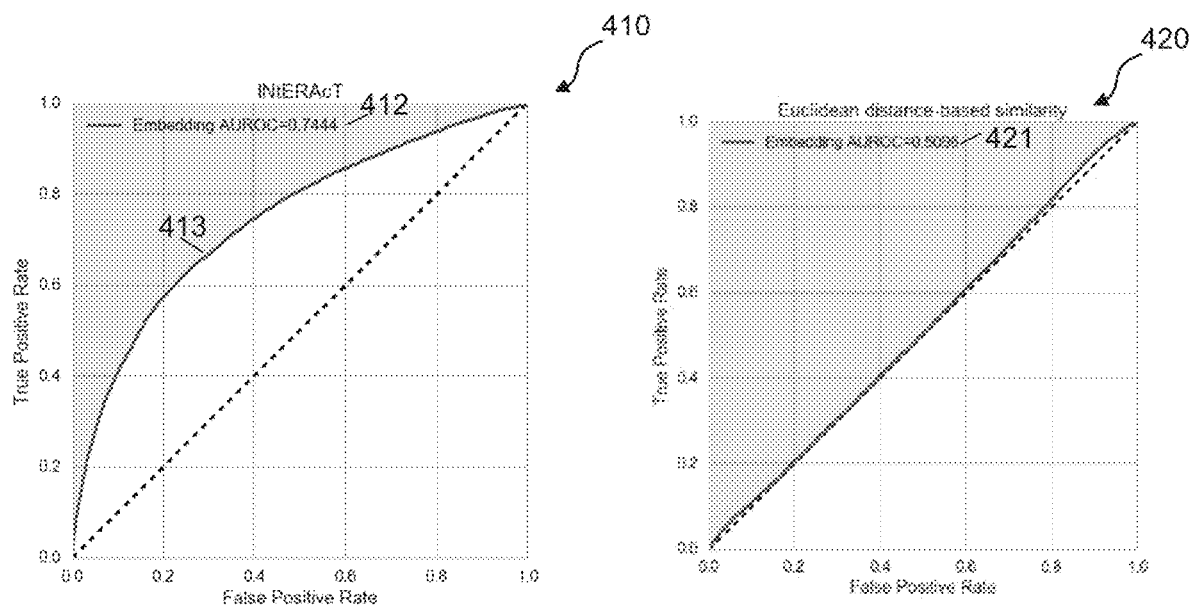
FIG. 4B depicts results of applying the present method on text elements obtained from prostate cancer publications.

FIGS. 4A-B depict results of applying the present method on text elements obtained from prostate cancer publications.

For example at least 180000 articles related to prostate cancer have been downloaded and parsed. After processing the articles, a dictionary composed of 25000 single words, bi-grams and tri-grams is obtained (e.g. the dictionary may be the obtained text elements of step 201). A word embedding algorithm (e.g. having 500 dimensions) may be applied on the 25000 text elements. Next a K-means clustering on the embedding with 500 clusters may be performed and the nearest neighbors may be accessed as described above. As described in FIGS. 3A-B, normalized neighborhood distributions (301A-C) of selected text elements may be used to calculate pairwise similarity scores. The calculation of the similarity scores may for example be done on a subset of text elements (e.g. the subset comprises a list of molecular entities).

To generate an interaction graph between molecular entities, a set of genes (collectively referred to as 401) may be used. For example the genes reported in the prostate cancer pathway as defined by the Kyoto Encyclopedia of Genes and Genomes5 (KEGG) may be used. 87 molecular entities from the KEGG prostate cancer pathway with the words from the prostate cancer corpus may be selected (e.g. to form the set of text elements of step 207). And 65 molecular entities of the corpus that are also part of the 87 molecular entities are used to compute the similarity scores as described above. The top 30 interactions from the resulting network or interaction graph 400 inferred using the present method are shown in FIG. 4A. The edges (collectively referred to as 403) between the nodes 401 (set of genes known to be important prostate cancer onset and development) were inferred using the present method to extract interactions from the word embedding space. The thickness of the edges 403 corresponds to the interaction strength. Each edge 403 may be assigned a weight that represents the confidence of each interaction between the molecules linked by the edge.

The comparison of the obtained edges 403 or strength values associated with the edges 403 with interactions between the same set of genes as reported in OmniPath (a comprehensive PPI built combining multiple databases) may be quantified using a receiver operating characteristic (ROC) plot or graph 410 of FIG. 4B. The ROC plot 410 shows the true positive rates versus false positive rates for different classification thresholds. While an interaction reported in OmniPath may be considered to be true, a non-reported interaction may be either true or false. Thus by enlarging the focus to a bigger set of interactions the ratio between TP and FP can only increase leading to a consequent increase in the area under the ROC curve 213 (AUROC) score 412. The AUROC score 412 may be defined as the sum of the areas between the x-axis and the curve 413 of the ROC plot 410. The ROC plot 410 indicates that the present method to infer molecular interactions from publications gives high similarity score to edges between entities with interactions contained in the OmniPath set of reported interactions compared to other methods. For example, by calculating the similarity scores using an Euclidean distance without building and using the groups and the distributions as with the present method, the obtained AUROC score may be smaller. The ROC plot 420 shows the result of the Euclidean distance based similarity with a smaller AUROC score 422 of 0.5.

In another example, a computer implemented method to automatically extract context specific information, in particular molecular interaction networks, from un-structured text data is provided. The method comprises: obtaining a plurality of text data; applying a word embedding algorithm; clustering the words in the embedding into groups conveying similar semantic meaning; extracting the context specific information, in particular the molecular interactions, from the embedding by computing similarity scores based on neighborhood distributions across groups.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer implemented method to extract information from text data, the method comprising:
   obtaining from a plurality of documents, using a hardware processor, a plurality of text elements comprising names of molecular entities;
   applying, using the hardware processor, a word embedding algorithm to the obtained text elements comprising mapping each text element of at least part of the text elements into a vector of a predefined dimension, wherein said mapping each text element comprises:
   receiving a text element input;
   training a model to predict the surrounding words of the input text element, said predict model training comprising:
   defining a window of predetermined size spanning an amount of words surrounding the text element to obtain a word context from a document,
   mapping a target word to its surrounding words within the window;
   feeding pairs of target-neighboring words into a neural network, said neural network trained to optimize a probability of a semantic meaning of a word given the obtained word context; and
   representing said received text element according to a real vector to capture said semantic meaning;
   clustering, using the hardware processor, the mapped text elements into groups using the distances between the respective vectors;
   building, using the hardware processor, for a set of text elements of the mapped text elements a respective distribution of neighbors across the groups;
   computing, using the hardware processor, similarity scores using the distributions thereby determining relations between the set of text elements, and
   building, using the hardware processor, a molecular interaction network using the similarity scores, said building an interaction network comprising:
   providing nodes corresponding to one or more text elements of the set of text elements in a graph structure;
   connecting edges between the nodes; and
   weighing the edges by the similarity score values of the nodes they connect, an edge weight representing a confidence of each interaction between the molecules linked by the edge.

2. The method of claim 1, further comprising providing a vocabulary of text elements, wherein the set of text elements are present in both the mapped text elements and the vocabulary.

3. The method of claim 1, the building of the distribution for a given text element comprising: identifying a predefined number of nearest neighbors of the given text element; determining the group to which belongs each of the identified nearest neighbors, wherein the distribution for the given text element indicates for each determined group the fraction of nearest neighbors of the identified nearest neighbors that belongs to the determined group over the predefined number of nearest neighbors.

4. The method of claim 3, wherein identifying the nearest neighbors comprises building a k-dimensional tree of the vectors representing the text elements and using the k-dimensional tree for identifying the nearest neighbors.

5. The method of claim 3, wherein the predefined number of nearest neighbors is determined based on the number of groups.

6. The method of claim 1, the obtaining of the text data comprising:
   querying a predefined database for one or more documents;
   parsing the queried documents for extracting text;
   identifying in the extracted text at least one of bi-grams, trigrams, words and a combination thereof for obtaining the text elements.

7. The method of claim 1, wherein the similarity scores are Jensen-Shannon divergence, JSD, scores which are computed for pairs of the built distributions.

8. The method of claim 1, wherein the clustering is performed using a K-means algorithm.

9. The method of claim 1, wherein the text elements form un-structured data.

10. The method of claim 1, being automatically performed.

11. A computer program product comprising a computer-readable storage medium having computer-readable program code embodied therewith, the computer-readable program code configuring a computer system to:
   obtain from a plurality of documents, a plurality of text elements comprising names of molecular entities;
   apply a word embedding algorithm to the obtained text elements comprising mapping each text element of at least part of the text elements into a vector of a predefined dimension, wherein to map each text element, said computer-readable program code further configuring said computer system to:

receive a text element input;

train a model to predict the surrounding words of the input text element, said predict model training comprising:

define a window of predetermined size spanning an amount of words surrounding the text element to obtain a word context from a document, map a target word to its surrounding words within the window;

feed pairs of target-neighboring words into a neural network, said neural network trained to optimize a probability of a semantic meaning of a word given the obtained word context; and represent said received text element according to a real vector to capture said semantic meaning;

cluster the mapped text elements into groups using the distances between the respective vectors;

build for a set of text elements of the mapped text elements a respective distribution of neighbors across the groups; and compute similarity scores using the distributions thereby determining relations between the set of text elements;

build a molecular interaction network using the similarity scores, wherein to build the molecular interaction network, said computer-readable program code further configuring said computer system to:

provide nodes corresponding to one or more text elements of the set of text elements in a graph structure;

connect edges between the nodes; and weigh the edges by the similarity score values of the nodes they connect, an edge weight representing a confidence of each interaction between the molecules linked by the edge.

12. A computer system to extract information from text data, the computer system comprising:

a processor; and a non-transitory computer-readable memory coupled to the processor, wherein the memory comprises instructions which, when executed by the processor, cause the processor to:

obtain from a plurality of documents, a plurality of text elements comprising names of molecular entities;

apply a word embedding algorithm to the obtained text elements comprising mapping each text element of at least part of the text elements into a vector of a predefined dimension, wherein to map each text element, said hardware processor is further configured to:

receive a text element input;

train a model to predict the surrounding words of the input text element, said predict model training comprising:

define a window of predetermined size spanning an amount of words surrounding the text element to obtain a word context from a document, map a target word to its surrounding words within the window;

feed pairs of target-neighboring words into a neural network, said neural network trained to optimize a probability of a semantic meaning of a word given the obtained word context; and represent said received text element according to a real vector to capture said semantic meaning;

cluster the mapped text elements into groups using the distances between the respective vectors;

build for a set of text elements of the mapped text elements a respective distribution of neighbors across the groups;

compute similarity scores using the distributions thereby determining relations between the set of text elements, and build a molecular interaction network using the similarity scores, wherein to build said interaction network between molecular entities of interest, the processor is further configured to perform:

providing nodes corresponding to one or more text elements of the set of text elements in a graph structure;

connecting edges between the nodes; and weighing the edges by the similarity score values of the nodes they connect, an edge weight representing a confidence of each interaction between the molecules linked by the edge.

13. The system of claim 12, wherein the set of text elements are present in both the mapped text elements and a vocabulary of text elements.

14. The system of claim 12, wherein the processor is configured to perform the building of the distribution for a given text element by: identifying a predefined number of nearest neighbors of the given text element; determining the group to which belongs each of the identified nearest neighbors, wherein the distribution for the given text element indicates for each determined group the fraction of nearest neighbors of the identified nearest neighbors that belongs to the determined group over the predefined number of nearest neighbors.

15. The system of claim 14, wherein the processor is configured for identifying the nearest neighbors by building a k-dimensional tree of the vectors representing the text elements and using the k-dimensional tree for identifying the nearest neighbors.

16. The system of claim 14, wherein the processor is configured to determine the predefined number of nearest neighbors based on the number of groups.

17. The system of claim 12, wherein the processor is configured for obtaining of the text data by:

querying a predefined database for one or more documents;

parsing the queried documents for extracting text;

identifying in the extracted text at least one of bi-grams, trigrams, words and a combination thereof for obtaining the text elements.

18. The system of claim 12, wherein the similarity scores are Jensen-Shannon divergence, JSD, scores which are computed for pairs of the built distributions.

* * * * *